(12) United States Patent
Hayashizaki

(10) Patent No.: US 6,458,556 B1
(45) Date of Patent: *Oct. 1, 2002

(54) METHOD FOR ENHANCING ENZYME ACTIVITY AT ELEVATED TEMPERATURE

(75) Inventor: Yoshihide Hayashizaki, Ibaraki (JP)

(73) Assignee: The Institute of Physical & Chemical Research, Saitama (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/899,393

(22) Filed: Jul. 23, 1997

(30) Foreign Application Priority Data

Jul. 25, 1996 (JP) .............................................. 8-196330

(51) Int. Cl.$^7$ ............................. C12N 9/00; C07K 14/00
(52) U.S. Cl. ........................ 435/41; 435/91.2; 435/183; 514/2; 514/451; 514/553; 530/350
(58) Field of Search ........................ 435/91.2, 41, 183; 514/2, 451, 553; 530/350

(56) References Cited

U.S. PATENT DOCUMENTS 5,614,387 A * 3/1997 Shen et al. ................. 435/91.2

FOREIGN PATENT DOCUMENTS

| EP | 0 035 204 | | 9/1981 |
|---|---|---|---|
| EP | 0 117 064 | | 8/1984 |
| JP | 4-370095 | | 12/1992 |
| JP | 5-268952 | | 10/1993 |
| JP | 8-131170 | | 5/1996 |
| WO | 0 117 064 | * | 8/1984 |
| WO | 93 16175 | | 8/1993 |
| WO | 96 15235 | | 5/1996 |

OTHER PUBLICATIONS

Thaker et al. 'Osmolyte Mediated of T7 DNA Polymerase and Plasmid DNA Stability', Biochemistry, vol. 33, pp. 12255–12259.*

Skowyra et al. 'The *E. Coli* Dnak Gene Product, The HSP70 Homolog, Can Reactive Heat Inactivated RNA Polymerase in an ATP Hydrolysis–Dependent Manner', Cell. vol. 62. pp. 939–944.*

Hottiger et al. 'The Role of Trehalose Synthesis for the Acquisition of Thermotolerance in Yeast II. Physiological Concentration of Trehalose Increase Thermal Stability of Proteins in Vitro' Eur. J. Biochem. vol. 219, pp. 187–193.*

Carninci et al., "Thermostabilization and Thermoactivation of Thermolabile Enzymes by Trehalose and Its Application for the Synthesis of Full Length cDNA" *Proc. Natl. Acad. Sci. USA*, vol. 95, pp. 520–524, Jan. 1998.

Burteau et al., "Stabilisation and Immobilisation of Penicillin Amidase", *FEBS Letters*, vol. 258, No. 2, Dec. 4, 1989, Amsterdam NL, pp. 185–189.

Bernier et al., "Stabilization of Beta–Galactosidase by Polyhydric Alcohols", *Journal of Biotechnology*, vol. 7, No. 4, 1988, Amsterdam NL, pp. 293–298.

"Enzyme Stabilization" *Advances in Biochemical Engineering*, vol. 12, Jan. 1, 1979, New York US, pp. 55–67.

Thaker, et al., "Osmolyte Mediation of T7 DNA Polymerase and Plasmid DNA Stability" Biochemistry, 1994, 33, 12255–12259.*

Mahoney, et al., Substrate–induced Thermal Stabilization of Lactase (*Escherichia coli*) in Milk, in Ann. New York Acad. Sci., 1988, 542, 274–278.*

Coolbear, et al., Proteases from Extreme Thermophiles in Ann. New York Acad. Sci., 1988, 542, 279–281.*

Larreta–garde, et al., "Behavior of Enzymes in the Presence of Additives", in Ann. New York Acad. Sci., 1988, 542, 294–298.*

Back, et al., "Thermal Stability of Proteins", Biochemistry, 1979, 18, 5191–5196.*

Buchner, et al., "GroE Facilitates Refolding of Citrate Synthase by Suppressing Aggregation", Biochemistry, 1991, 30, 1586–1591.

Klibanov, A., "Stabilizationof Enzymes Against Thermal Inactivation" in Adv. Appl. Microbiology, 1983, Academic Press: New York, vol. 29, 1–28.

Colaco, et al., "Extraordinary Stability of Enzymes Dried in Trehalose: Simplified Molecular Biology", Bio/Technology, 1992, 10 (9), 1007–1011.

* cited by examiner

*Primary Examiner*—Christopher S. F. Low
*Assistant Examiner*—Anish Gupta
(74) *Attorney, Agent, or Firm*—Burns, Doane, Swecker & Mathis, L.L.P.

(57) ABSTRACT

A method for enhancing activity of enzyme at an elevated temperature which comprises adding a substance exhibiting chaperone function such as a saccharide to a reaction mixture containing the enzyme. The method can improve activity of enzymes more easily and more effectively and hence afford increased enzyme activity at an elevated temperature.

14 Claims, 5 Drawing Sheets

FIG. 1

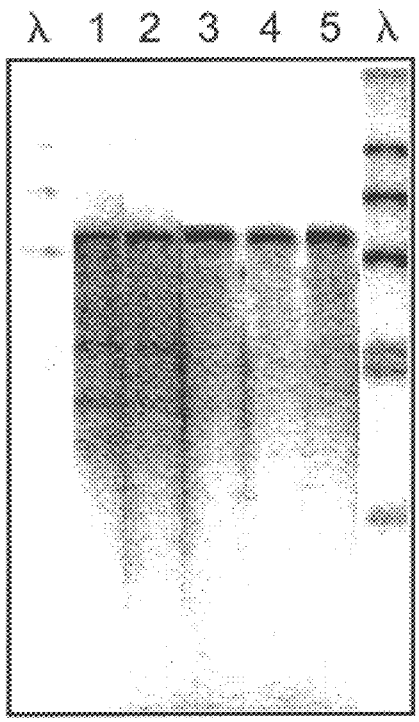

λ= Lambda HinDIII marker
1) Standard "optimized" buffer condition: Reaction temperature 42°C
2) Buffer containing trehalose (20%) and glycerol (20%):
   Reaction temperature 42°C
3) Buffer containing trehalose (20%) and glycerol (20%):
   Reaction temperature 60°C
4) Buffer containing trehalose (20%), glycerol (20%) and Triton
   X-100 (0.05%): Reaction temperature 60°C
5) Buffer containing trehalose (20%), glycerol (20%) and BSA
   (125 ng/μl): Reaction temperature 60°C Superscript II is inactivated at a temperature of 50°C or more
under the standard buffer condition (not shown).

1) 17) λHind III
2) 37°C       0 M
3) 37°C     0.2M
4) 37°C     0.6M
5) 45°C       0 M
6) 45°C     0.2M
7) 45°C     0.6M
8) 50°C       0 M
9) 50°C     0.2M
10) 50°C    0.6M
11) 55°C      0 M
12) 55°C    0.2M
13) 55°C    0.6M
14) 60°C      0 M
15) 60°C    0.2M
16) 60°C    0.6M 1) λHind III
2) 37 °C    0 M
3) 37 °C    0. 2M
4) 37 °C    0. 6M
5) 37 °C    1. 2M
6) 37 °C    2. 4M
7) 37 °C    3. 6M
8) 45 °C    0  M
9) 45 °C    0. 2M
10) 45 °C   0. 6M
11) 45 °C   1. 2M
12) 45 °C   2. 4M
13) 45 °C   3. 6M
14) 50 °C    0 M
15) 50 °C   0. 2M
16) 50 °C   0. 6M
17) 50 °C   1. 2M
18) 50 °C   2. 4M
19) 50 °C   3. 6M
20) 55 °C    0 M
21) 55 °C   0. 2M
22) 55 °C   0. 6M
23) 55 °C   1. 2M
24) 55 °C   2. 4M
25) 55 °C   3. 6M

METHOD FOR ENHANCING ENZYME ACTIVITY AT ELEVATED TEMPERATURE

BACKGROUND OF THE INVENTION

The present invention relates to a method for enhancing enzyme activity at an elevated temperature by using a substance exhibiting chaperone function.

In general, enzymes exhibit lower activity at a temperature above their optimum temperature than the activity at their optimum temperature. It is also known that their activity is lost when they are exposed to a temperature higher than a certain level. Depending on the kind of enzyme, a temperature at which such heat inactivation occurs may vary. However, most of enzymes having optimum temperature of ordinary temperature are inactivated when heated to around 50° C. Enzymes stable at an elevated temperature are also known and such heat-resistant enzymes generally have a higher optimum temperature.

Depending on the conditions where enzymes are used, it is often desirable to use enzymes at an elevated temperature. In such a case, a heat-resistant enzyme as mentioned above is generally used. Examples of such a heat-resistant enzyme include Taq polymerase, which is frequently used for PCR. However, in many cases, a suitable heat-resistant enzyme may not be known, or even if a possible heat-resistant enzyme is known, other conditions to be used may not meet the enzyme.

For example, Superscript II is known as a reverse transcriptase (RNA-dependent DNA polymerase) which can afford a cDNA from a mRNA in vitro. Superscript II is a heat-labile enzyme exhibiting an optimum temperature of 42° C. and completely inactivated at a temperature above 50° C. within 10 minutes. Although Tth DNA polymerase is an enzyme having heat resistance and reverse transcription activity, it requires manganese ions for exerting the enzyme activity. If cDNAs are produced from mRNAs at a higher temperature using the Tth DNA polymerase, mRNAs are fragmented by manganese ions presented in a reaction system and therefore it becomes difficult to obtain full length cDNAs.

Magnesium ions required by a heat-labile reverse transcriptase such as Superscript II mentioned above may also cause the fragmentation of mRNA in a certain buffer or water at an elevated temperature. According to the present inventor's researches, manganese ions exhibit stronger fragmentation activity than magnesium ions and control of the fragmentation due to manganese ions is difficult even using a chelating agent.

Taq polymerase is known as an inherently heat-resistant enzyme. However, it shows reduction of activity during 25 to 30 cycles or more generally used in PCR. Therefore, if the reduction of Taq polymerase activity can be prevented, higher amplification effect and higher cycle number can be realized with fewer units of the enzyme.

In some cases, reverse transcription may be required to be performed at a temperature above 50° C. for some reasons. For example, in order to obtain full length cDNAs, it is desirable to preform reverse transcription while preventing the formation of secondary structure of mRNAs.

However, a heat-resistant enzyme having reverse transcription activity such as Tth DNA polymerase cannot afford full length cDNAs. Therefore, it is necessary to utilize a currently available reverse transcriptase which is used at an ambient temperature.

Similar situation may be frequently found in other enzymes not only polymerases but also restriction enzymes.

For some enzymes, it has been known that an enzyme exhibiting a higher optimum temperature can be obtained by introducing a mutation through genetic engineering. However, such improvement of heat-resistance is not always possible and has not been known so long as reverse transcriptase concerns.

If an enzyme can exhibit higher activity at a higher temperature, its utility may be enhanced even though it is known as a heat resistant enzyme.

Therefore, the object of the present invention is to provide a method for easily and efficiently improving heat resistance of enzyme to obtain high enzyme activity at an elevated temperature.

DESCRIPTION OF THE INVENTION

The present invention provides a method for enhancing activity of enzyme which comprises adding a substance exhibiting chaperone function to a reaction mixture containing the enzyme.

FIG. 1 is a photograph showing the results of agarose gel electrophoresis obtained in Example 1.

Figure 4:
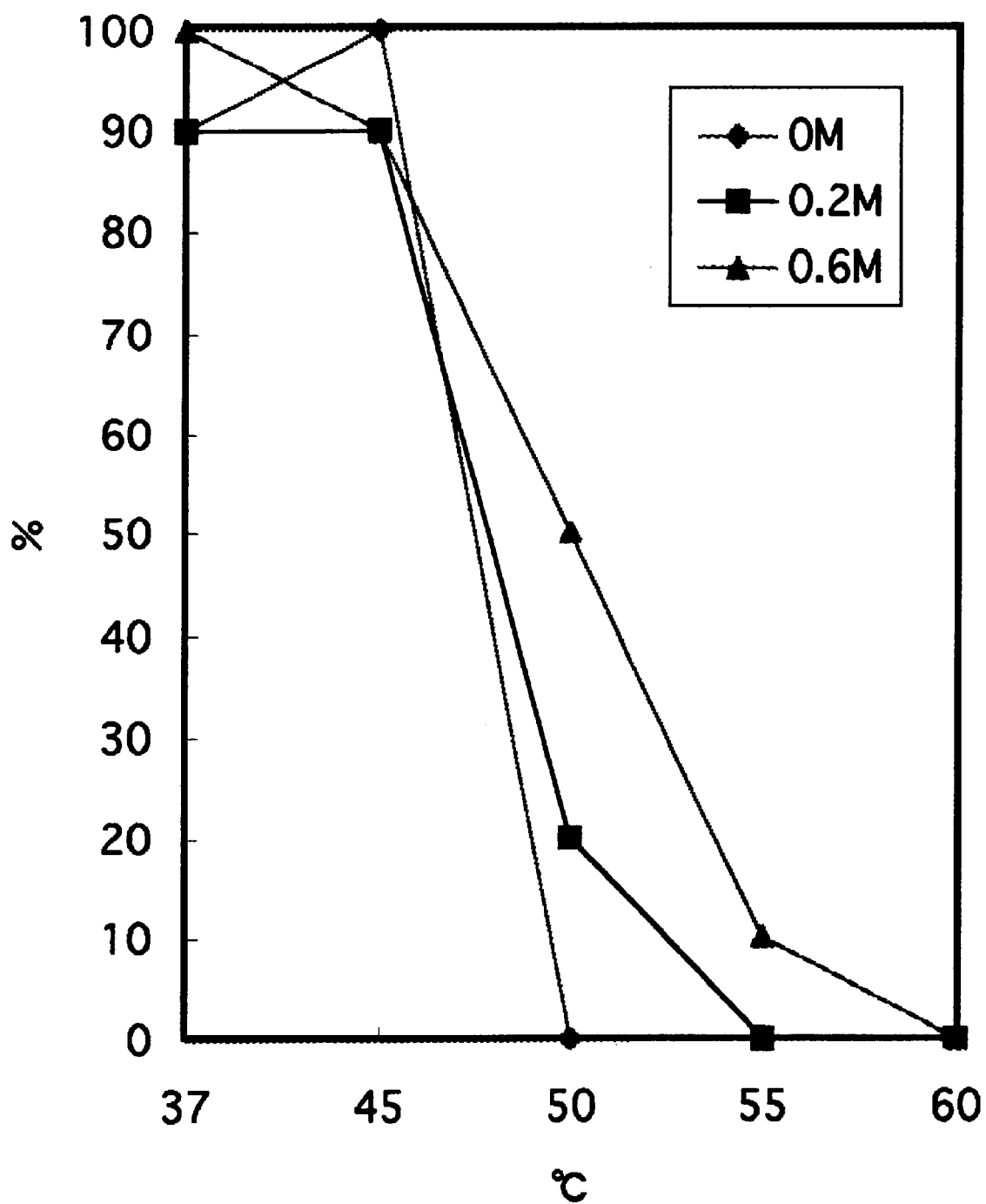

FIG. 4 presents relative activity of Sty I tested in Example 4 in which betain was used.

Figure 5:
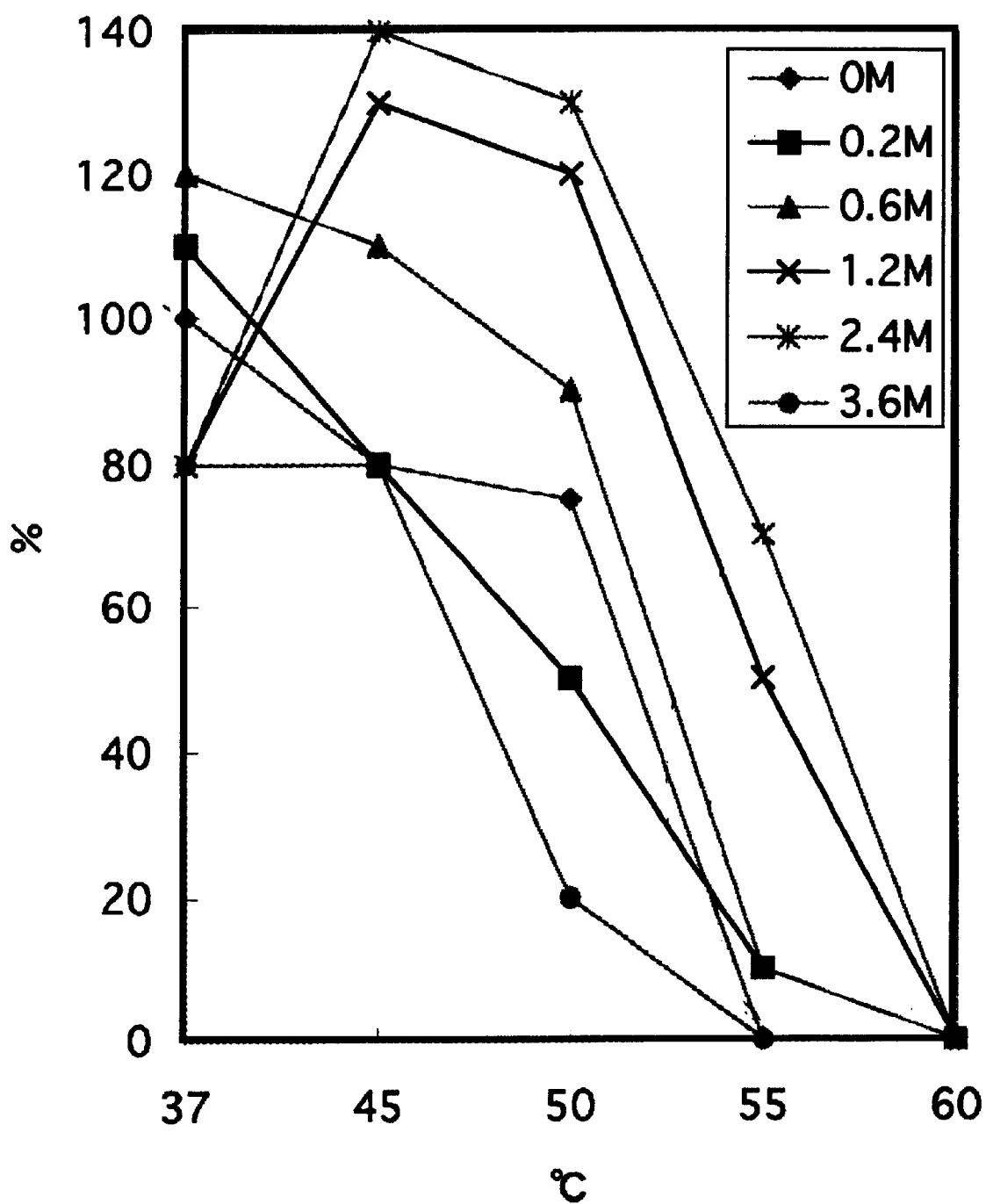

FIG. 5 presents relative activity of Sty I tested in Example 4 in which sarcosine was used.

In the method of the present invention, the objective enzyme is not particularly limited and may be an enzyme which is not inactivated and exhibits its activity at an elevated temperature. It may be possible to enhance an activity of enzyme at a higher temperature by applying the method of the present invention to an enzyme which is not permanently inactivated but exhibit substantially no activity or which is inactivated at an elevated temperature under ordinary conditions, so long as they are in a condition where activation at an elevated temperature is possible.

Typical examples of the enzyme to which the method of the present invention is applicable include polymerases and restriction enzymes. Examples of polymerases include DNA polymerases, RNA-dependent DNA polymerases (reverse transcriptases), DNA replicases, terminal deoxytransferases, poly A polymerases and telomerases. However, the enzyme is not limited to these.

Examples of the DNA polymerase include Sequencease Ver.2, T7 DNA polymerase, T4 DNA polymerase, DNA polymerase I and the like. Examples of the heat-resistant, DNA polymerase include Taq polymerase, Vent DNA polymerase, pfu polymerase, Tth polymerase, Thermosequenes and the like. Heat resistance of these heat resistant DNA polymerases can be further enhanced by the method of the present invention and therefore amplification ratio and cycle number of PCR can be increased to improve stability of PCR.

Examples of the RNA-dependent DNA polymerase (reverse transcriptase) include Seperscript II, AMV reverse transcriptase, MulV reverse transcriptase and the like.

In addition to such polymerases as mentioned above, some restriction enzymes such as Taq I are not inactivated and exhibit substantial activity at an elevated temperature. Such enzymes may also be stabilized at an elevated temperature by the method of the present invention. Examples of restriction enzymes to which the method of the present invention is applicable include Sty I, Eco RI, Mlu I, Nco I, DNase I, Rnase I, Nde I, Pvu II, Pst I, Dra I, Hin DIII and Hin cII. However, the enzyme is not limited to these.

In the method of the present invention, a substance exhibiting chaperone function is presented in a reaction mixture.

Examples of the substance exhibiting chaperone function include saccharides, amino acids, polyalcohols and their derivatives, and chaperone proteins. However, the substance is not limited to these. The "chaperone function" means a function for renaturing proteins denatured by stress such as heat shock, or a function for preventing complete denaturation of proteins by heat to maintain the native structure.

Examples of the saccharide exhibiting the chaperone function include oligosaccharides and monosaccharides such as trehalose, maltose, glucose, sucrose, lactose, xylobiose, agarobiose, cellobiose, levanbiose, quitobiose, 2-β-glucuronosylglucuronic acid, allose, altrose, galactose, gulose, idose, mannose, talose, sorbitol, levulose, xylitol and arabitol. However, the saccharide is not limited to these. Those saccharides mentioned above can be used alone or in any combination thereof. Among these, trehalose, sorbitol, xylitol, levulose and arabitol exhibit strong chaperone function and marked effect for activating enzymes at an elevated temperature.

Examples of the amino acids and derivatives thereof include $N^\varepsilon$-acetyl-β-lysine, alanine, γ-aminobutyric acid, betaine, $N^\alpha$-carbamoyl-L-glutamine 1-amide, choline, dimethylthetine, ecotine (1,4,5,6-tetrahydro-2-methyl-4-pirymidine carboxilic acid), glutamate, β-glutammine, glycine, octopine, proline, sarcosine, taurine and trymethylamine N-oxide (TMAO). However, the amino acids and derivatives thereof are not limited to these. Those amino acids mentioned above can be used alone or in any combination thereof. Among these, betaine and sarcosine exhibit strong chaperone function and marked effect for activating enzymes at an elevated temperature.

The substance exhibiting chaperone function include polyalcohols. The saccharides are included in polyalcohols and other examples of the polyalcohols include glycerol, ethylene glycol, polyethylene glycol and the like. Those polyalcohols can be used alone or in any combination thereof.

The substance exhibiting chaperone function include chaperone proteins. Examples of the chaperone proteins include chaperone proteins of Thermophilic bacteria and heat shock proteins such as HSP 90, HSP 70 and HSP 60. Those chaperone proteins can be used alone or in any combination thereof.

These substances exhibiting chaperone function show different optimum concentrations for stabilizing the enzyme depending on the kind of the enzyme and the optimum concentration may vary among the substances for the same enzyme. Therefore, a concentration of particular substance to be added to a specific reaction system may be suitably decided depending on the kinds of the substance and the enzyme such as reverse transcriptase.

To enhance the effect of the substances exhibiting chaperone function such as saccharides, amino acids or chaperone proteins, one or more kinds of polyalcohols may be used in addition to one ore more kinds of the above substances. Examples of the polyalcohol include glycerol, ethylene glycol, polyethylene glycol and the like.

According to the method of the present invention, activity of enzyme such as a polymerase or a restriction enzyme can be enhanced at an elevated temperature. The term "elevated temperature" herein used refers to, for example, a temperature of 45 to 110° C. However, the temperature at which an enzyme can be stabilized may be vary depending on the kind of the enzyme. An enzyme usually used at an ordinary temperature may be stabilized at an elevated temperature higher than ordinary temperature, and a heat-resistant enzyme can be stabilized at a further elevated temperature higher than its optimum temperature.

According to the method of the present invention, not only heat-resistance of enzymes such as polymerases and restriction enzymes can be improved, but also activity of enzymes such as polymerases and restriction enzymes at an elevated temperature can be enhanced by using the above-mentioned substance exhibiting chaperone function.

EXAMPLES

The present invention will be further explained in detail with reference to the following examples.

Example 1

Improvement of Reverse Transcription Efficiency by Making Reverse Transcriptase Heat-resistant To examine reverse transcription activity of Superscript II at an elevated temperature, cDNAs were synthesized using RNAs transcribed in vitro by T7 RNA polymerase as template and the products were evaluated. By using RNAs as a template transcribed in vitro and evaluating the products by electrophoresis, reverse transcription efficiencies of the samples can be compared with one another and thereby non-specific transcription termination which leads to premature termination of reverse transcription and/or reduction of reaction efficiency can be evaluated. The template RNAs were prepared by transcribing pBluescript II SK, which had been cleaved into a linear form with a restriction enzyme NotI, with T7 RNA polymerase in vitro. This reaction was initiated from T7 promoter described in the instruction of pBluescript II SK.

As a control, the following standard buffer condition was used: 50 mM Tris-HCl, pH 8.3, 75 mM KCl, 3 mM $MgCl_2$, 10 mM dithiothreitol, each 0.75 mM of dNTPs (dATP, dGTP, dCTP and dTTP).

In the above standard buffer condition, 1 µg of template RNA, 400 µg of primer (20 mer SK primer and 200 units of Superscript II were prepared and the final volume was adjusted to 20 µl. 0.2 µl of [α-$^{32}$P] dGTP was used for labeling of reverse transcription products. The RNA and the primer were incubated at 65° C. before the other substrates were added. Then, the reaction was performed at 42° C. for 1 hour. The reaction products were subjected to denatured agarose electrophoresis and electrophoretic patterns were examined by autoradiography to evaluate recoveries of full length cDNAs and rates of short products obtained from incomplete elongation. The results are shown in Lane 1 of FIG. 1.

The reverse transcriptase Superscript II was inactivated at a temperature of 50° C. in the above standard buffer condition.

The following buffer condition for reverse transcription was used to verify that addition of oligosaccharide stabilizes the enzyme reaction: 50 mM Tris-HCl, pH 8.3, 75 mM KCl, 3 mM $MgCl_2$, 10 mM dithiothreitol, each 0.75 mM of dNTPs (dATP, dGTP, dCTP, dTTP), 20% (w/v) trehalose and 20% (v/v) glycerol.

1 µg of template RNA, 400 ng of primer (20 mer SK primer) and 200 units of Superscript II were reacted in 24 µl of aqueous solution under the above buffer condition. 0.2 µl of [α-$^{32}$P] dGTP was used for labeling of reverse transcription products. Under this condition, the reverse transcriptase Superscript II exhibited higher activity than the control reaction at a normal temperature (42° C.). The primer and the template RNAs were annealed at 37° C. for 2 minutes and the enzyme activity was measured at 60° C.

The reaction products were subjected to denaturing agarose electrophoresis as described above, and electrophoretic patterns were examined by autoradiography to evaluate recoveries of full length cDNAs and rates of short products obtained from incomplete elongation. The results are shown in FIG. 1.

As shown in Lane 1, products resulted from premature termination of reverse transcription at specific sites or non-specific termination of reverse transcription were seen under the standard buffer condition at 42° C.

As shown in Lane 2, at 42° C. as in Lane 1, such products resulted from premature termination as mentioned above were also observed even though 20% trehalose and 20% glycerol were added.

As shown in Lane 3, when the temperature was raised to 60° C., the amount of products obtained from prematurely terminated synthesis became very small and full length products were synthesized.

As shown in Lane 5, when 0.125 µg/µl of BSA was added to the condition of Lane 3, the enzyme activity was further stabilized. However, BSA alone without 20% trehalose and 20% glycerol did not make the enzyme sufficiently heat-resistant.

As shown in Lane 4, when 0.05% of Triton X100 was added to the condition of Lane 3, the amount of incomplete reverse transcription products was further reduced. However, the whole activity of the reverse transcriptase was slightly reduced.

Example 2

Reaction was performed under the same condition as Lane 3 of Example 1 except that glucose or maltose was used instead of trehalose. The electrophoretic pattern showed again that the amount of products obtained from prematurely terminated synthesis became very small and full length products were synthesized as in Lane 3 of Example 1.

Example 3

Reaction was performed under the same condition as Lane 3 of Example 1 except that arabitol, sorbitol, levulose, xylitol or betaine was used instead of trehalose. The electrophoretic pattern showed again that the amount of products obtained from prematurely terminated synthesis became very small and full length products were synthesized as in Lane 3 of Example 1.

Example 4

Figure 2:
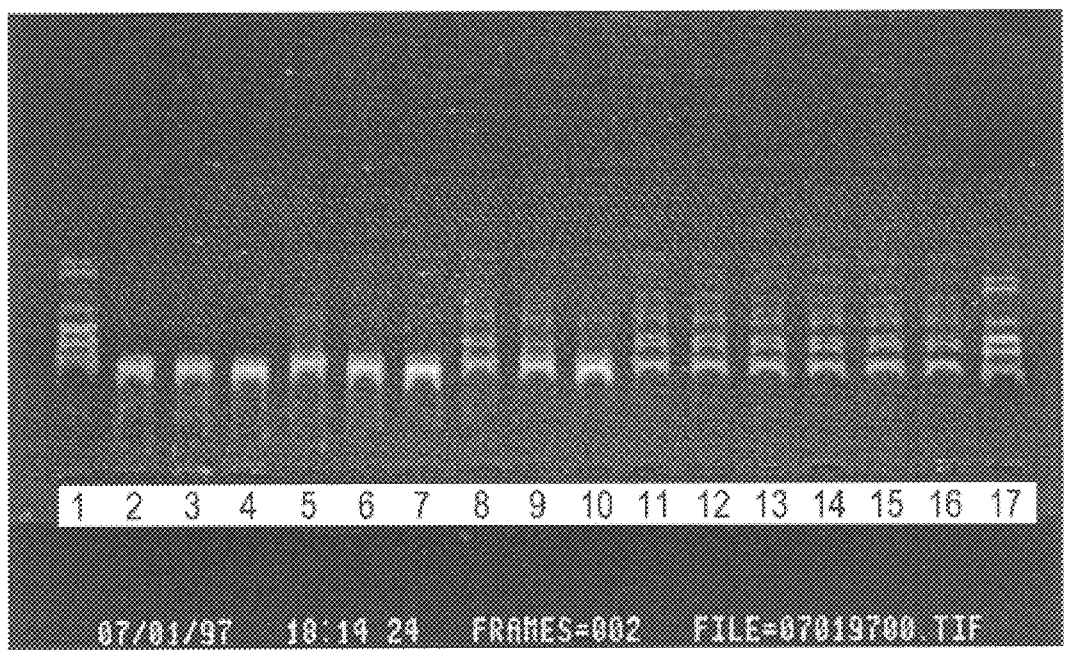
FIG. 2 is a photograph showing the results of agarose gel electrophoresis obtained in Example 4 in which betaine was used.
Figure 3:
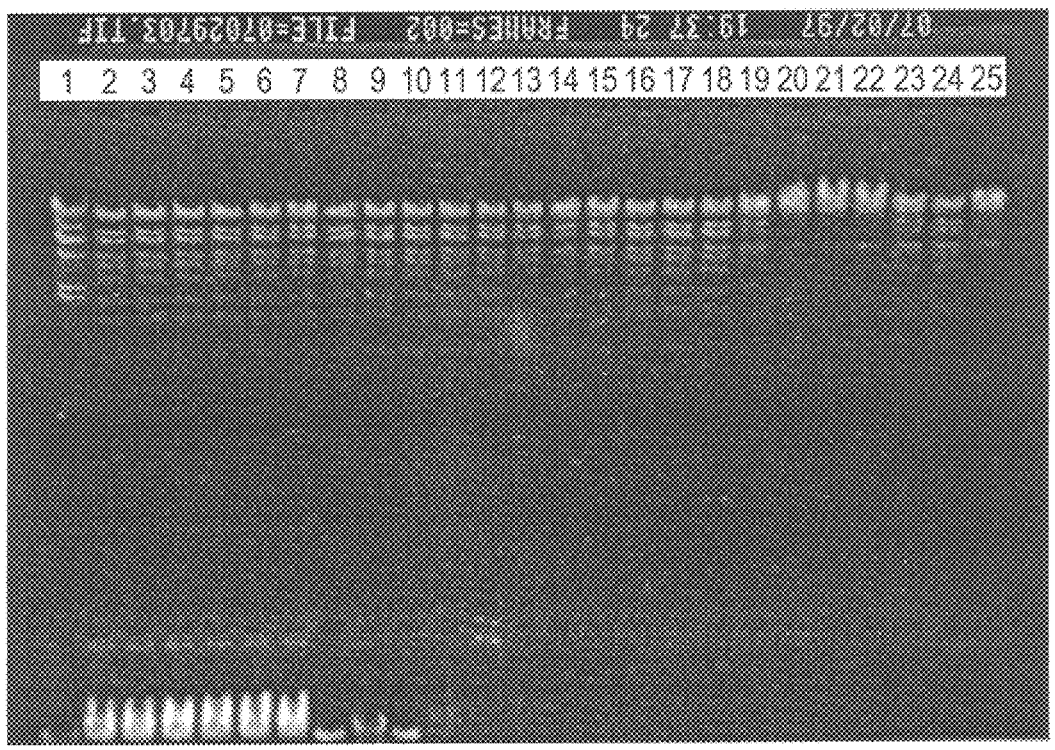
FIG. 3 is a photograph showing the results of agarose gel electrophoresis obtained in Example 4 in which sarcosine was used.

Reaction solutions (20 µl each) containing a restriction enzyme, Sty I 0.5 units, its substrate, λDNA 0.5 µg and betaine 0–0.6M or sarcosine 0–3.6M were incubated at 37, 45, 50, 55 or 60° C. for 1 hour. In order to prevent initiation of enzyme reaction before the incubation, the samples were quickly prepared on ice. Upon incubation, 0.25% bromophenol blue, 0.26% XC (xylene cyanol), 30% glycerol and 120 mM EDTA (4 µl) was added to the reaction solution to terminate the reaction. The resulting solution was heated at 65° C. for 5 minutes to melt cos sites and subjected to electrophoresis using 0.8% agarose gel containing 0.05% EtBr. A photograph showing the results of agarose gel electrophoresis regarding the samples using betin is presented in FIG. 2. A photograph showing the results of agarose gel electrophoresis regarding the samples using sarcosine is presented in FIG. 3.

After electrophoresis, image analysis of the gels was conducted. Enzyme activity was represented by comparing strength of bands appeared at 1 kbp (with arrow). Regarding the samples using betaine, the standard (100) is the band strength obtained from the sample using 0M of betaine and incubated at 37° C. Relative activity of Sty I tested in the presence of betaine is presented in FIG. 4. Regarding the samples using sarcosine, the standard (100) is the band strength obtained from the sample using 0 M of sarcosine and incubated at 37° C. Relative activity of Sty I tested in the presence of sarcosine is presented in FIG. 5.

From the results, it can be seen that a restriction enzyme was thermally activated by the addition of suitable concentration of betaine or sarcosine.

What is claimed is:

1. A method for enhancing polymerase or restriction activity of a polymerase or a restriction enzyme in a liquid reaction mixture at a temperature of 45 to 110° C., which comprises providing a liquid reaction mixture comprising a polymerase or restriction enzyme; and adding to said liquid reaction mixture a substance exhibiting chaperone function, wherein said activity enhancement is indicated by the presence of activity measured at a temperature at which said enzyme would normally be heat-inactivated and said activity being higher than the activity that said enzyme would show at a temperature at which said enzyme would normally not be heat-inactivated.

2. The method of claim 1, wherein the substance exhibiting chaperone function is one or more substances selected from the group consisting of saccharides, polyalcohols, amino acids and their derivatives, and chaperone proteins.

3. The method of claim 2, wherein the saccharide is one or more saccharides selected from the group consisting of trehalose, maltose, glucose, sucrose, lactose, xylobiose, agarobiose, cellobiose, levanbiose, quitobiose, 2-β-glucuronosylglucuronic acid, allose, altrose, galactose, gulose, idose, mannose, talose, sorbitol, levulose, xylitol and arabitol.

4. The method of claim 3, wherein the saccharide is trehalose sorbitol, levulose, xylitol or arabitol.

5. The method of claim 2, wherein the amino acid or derivative thereof is one or more members selected from the group consisting of $N^\epsilon$-acetyl-β-lysine, alanine, γ-aminobutyric acid, betain, $N^\alpha$-carbamoyl-L-glutamine 1-amide, choline, dimethylthetine, ecotine, glutamate, β-glutammine, glycine, octopine, proline, sarcosine, taurine and trymethylamine N-oxide.

6. The method of claim 5, wherein the amino acid or derivative thereof is betaine or sarcosine.

7. A method for enhancing polymerase or restriction activity of a polymerase or a restriction enzyme in a reaction mixture at a temperature of 45 to 110° C., which comprises providing a reaction mixture comprising a polymerase or a restriction enzyme; and adding a substance exhibiting chaperone function to the reaction mixture, wherein the substance exhibiting chaperone function is one or more substances selected from the group consisting of saccharides, polyalcohols, amino acids and their derivatives, and chaperone proteins selected from chaperone proteins of Thermophilic bacteria, and heat shock proteins, and wherein said activity enhancement is indicated by the presence of activity measured at a temperature at which said enzyme would normally be heat-inactivated and said activity being higher than the activity that said enzyme would show at a temperature at which said enzyme would normally not be heat-inactivated.

8. The method of claim 1, wherein one or more polyalcohols are added to the reaction mixture.

9. The method of claim 1, wherein the polymerase is a reverse transcriptase or DNA polymerase.

10. A method for enhancing polymerase or restriction activity of an enzyme in a liquid reaction mixture at a temperature of 45 to 110° C. which comprises providing a liquid reaction mixture comprising an enzyme; and adding trehalose to the liquid reaction mixture, wherein said activity enhancement is indicated by the presence of activity measured at a temperature at which said enzyme would normally be heat-inactivated and said activity being higher than the activity that said enzyme would show at a temperature at which said enzyme would normally not be heat-inactivated.

11. The method of claim 10, wherein one or more polyalcohols are further added to the liquid reaction mixture.

12. A method for enhancing polymerase or restriction activity of an enzyme in a liquid reaction mixture at a temperature of 45 to 110° C. which comprises providing a liquid reaction mixture comprising an enzyme; and adding betaine or sarcosine to the liquid reaction mixture, wherein said activity enhancement is indicated by the presence of activity measured at a temperature at which said enzyme would normally be heat-inactivated and said activity being higher than the activity that said enzyme would show at a temperature at which said enzyme would normally not be heat-inactivated.

13. The method of claim 12, wherein one or more polyalcohols are further added to the reaction mixture.

14. A method for enhancing polymerase or restriction activity of a polymerase or a restriction enzyme in a reaction mixture at a temperature of 45 to 110° C., which comprises:

providing a liquid reaction mixture comprising an enzyme; and adding a substance exhibiting chaperone function to the reaction mixture, wherein the substance exhibiting chaperone function comprises a chaperone protein selected from chaperone proteins of Thermophilic bacteria and heat shock proteins, and wherein said activity enhancement is indicated by the presence of activity measured at a temperature at which said enzyme would normally be heat-inactivated and said activity being higher than the activity that said enzyme would show at a temperature at which said enzyme would normally not be heat-inactivated.

* * * * *